US012622764B1

(12) United States Patent
Downs

(10) Patent No.: US 12,622,764 B1
(45) Date of Patent: May 12, 2026

(54) SURGICAL TRAY PROTECTOR

(71) Applicant: Anthony Kenneth Downs, Harrison Township, MI (US)

(72) Inventor: Anthony Kenneth Downs, Harrison Township, MI (US)

( * ) Notice: Subject to any disclaimer, the term of this patent is extended or adjusted under 35 U.S.C. 154(b) by 0 days.

(21) Appl. No.: 18/885,578

(22) Filed: Sep. 14, 2024

Related U.S. Application Data

(60) Provisional application No. 63/540,670, filed on Sep. 27, 2023.

(51) Int. Cl.
*A47G 11/00* (2006.01)
*A61B 50/33* (2016.01)
*A61B 50/00* (2016.01)

(52) U.S. Cl.
CPC ........ *A61B 50/33* (2016.02); *A61B 2050/002* (2016.02); *A61B 2050/0085* (2016.02)

(58) Field of Classification Search
CPC ......... A61B 46/00; A61B 46/10; A61B 50/13; A61B 2050/155; A61B 50/33; A61B 17/06114; A61B 50/00; A61B 50/30; A61B 50/31; A61B 5/002; A61B 2050/002; A61B 2050/0085; A47G 11/004

USPC ............................. 206/438; 128/849; 108/90
See application file for complete search history.

(56) References Cited

U.S. PATENT DOCUMENTS

| | | | | |
|---|---|---|---|---|
| 5,697,302 | A | * 12/1997 | Putnam | A47B 55/02 |
| | | | | 108/90 |
| 7,104,201 | B2 | * 9/2006 | Comeaux | A61B 50/13 |
| | | | | 108/90 |
| 2003/0233964 | A1 | 12/2003 | Comeaux | |
| 2004/0194673 | A1 | * 10/2004 | Comeaux | A47G 11/004 |
| | | | | 108/90 |
| 2006/0282051 | A1 | 12/2006 | Reichheld et al. | |

* cited by examiner

*Primary Examiner* — King M Chu
(74) *Attorney, Agent, or Firm* — Maiorana Patent Law, PA

(57) ABSTRACT

The invention concerns an apparatus comprising a sterile cover and a protective cover. The sterile cover may be configured to prevent a contamination of a surface. The protective cover may be configured to fit over a first portion of the sterile cover and provide protection against a sharp edge piercing the sterile cover. The first portion of the sterile cover may be within the protective cover. A second portion of the sterile cover creates an open end that may extend out of an open edge of the protective cover. The open end and the open edge may enable the sterile cover and the protective cover to slide over a top side and a bottom side of the surface together. An attachment may connect the protective cover to the sterile cover.

14 Claims, 6 Drawing Sheets

SURGICAL TRAY PROTECTOR

This application relates to U.S. Provisional Application No. 63/540,670, filed on Sep. 27, 2023, which is hereby incorporated by reference in its entirety.

FIELD OF THE INVENTION

The invention relates to a sterile product generally and, more particularly, to a method and/or apparatus for implementing a surgical tray protector.

BACKGROUND

Surgery requires a sterile environment and sterile tools. Ensuring a sterile environment can be time consuming for workers. Ensuring a sterile environment can be wasteful because tools determined to be non-sterile are disposed.

Surgical staff prepare the surgical room and the surgical instruments before a surgery occurs. Surgical trays for holding the surgical instruments are covered to ensure the surgical instruments remain sterile. If the surgical instruments directly make contact with the surface of the surgical tray, then the surgical instruments are considered contaminated and must be disposed.

Sterile covers are used to cover surgical trays to prevent direct contact between the surgical instruments and the surface of the surgical tray. However, sterile covers are not robust and surgical instruments are often sharp. If a surgical instrument pierces the sterile cover, then there is a risk of contamination, which requires the surgical instruments to be disposed and replaced. Disposing and replacing the surgical instruments is costly, and adds time, which can delay important medical procedures.

It would be desirable to implement a surgical tray protector.

SUMMARY

The invention concerns an apparatus comprising a sterile cover and a protective cover. The sterile cover may be configured to prevent a contamination of a surface. The protective cover may be configured to fit over a first portion of the sterile cover and provide protection against a sharp edge piercing the sterile cover. The first portion of the sterile cover may be within the protective cover. A second portion of the sterile cover creates an open end that may extend out of an open edge of the protective cover. The open end and the open edge may enable the sterile cover and the protective cover to slide over a top side and a bottom side of the surface together. An attachment may connect the protective cover to the sterile cover.

BRIEF DESCRIPTION OF THE FIGURES

Embodiments of the invention will be apparent from the following detailed description and the appended claims and drawings.

DETAILED DESCRIPTION OF THE EMBODIMENTS

Figure 1:
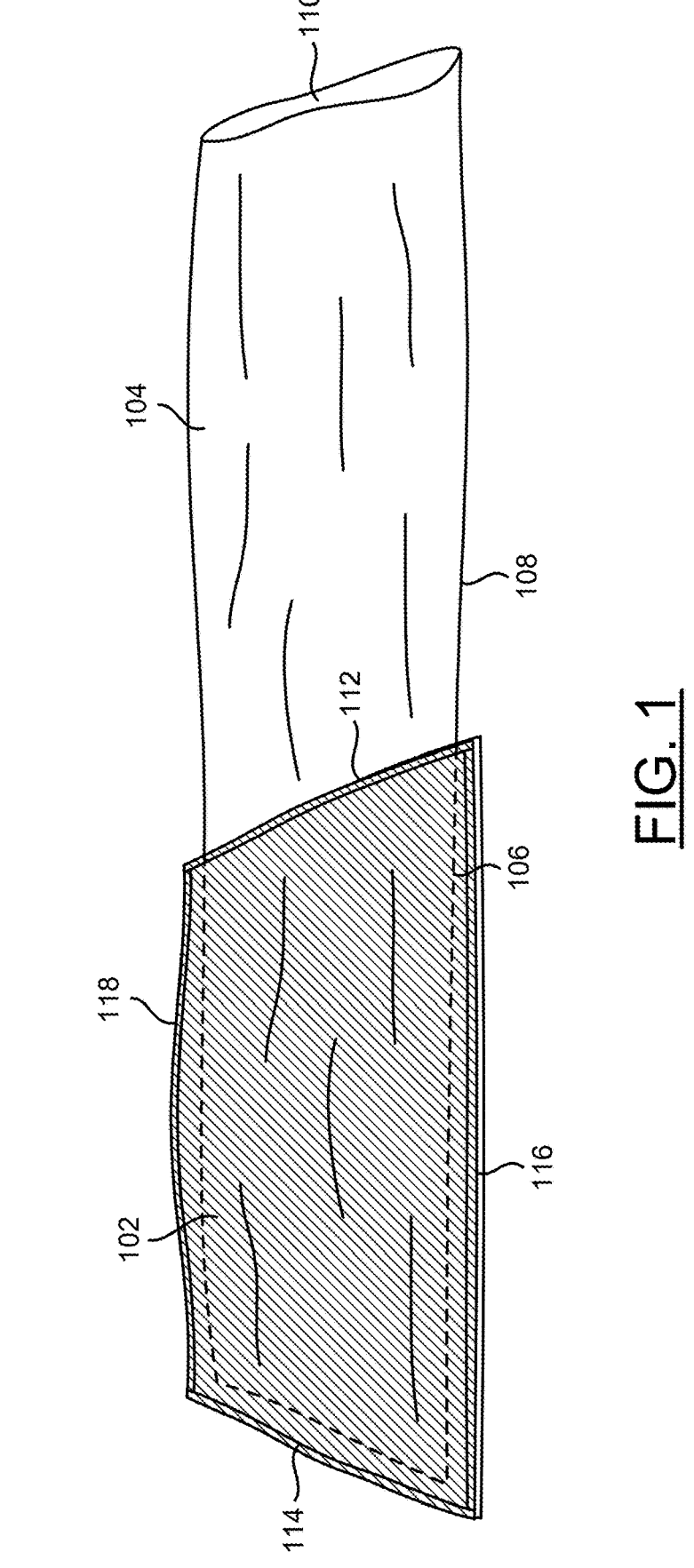
FIG. 1 is a diagram illustrating an example embodiment of the present invention.

Embodiments of the present invention include providing a surgical tray protector that may (i) implement a protective cover for a sterile cover, (ii) prevent surgical instruments from piercing a sterile cover, (iii) enable surgical staff to quickly install the sterile cover over a surgical tray, (iv) be implemented as a single piece, (v) attach a protective cover to a sterile cover, (vi) implement an adhesive to connect a protective cover to a sterile cover, (vii) prevent wasteful disposal of surgical tools, and/or (viii) facilitate efficient surgical room preparation for health workers.

Embodiments of the present invention may be implemented as one piece that may comprise a protective cover and a sterile cover. The protective cover may be attached together with the sterile cover. When attached together as one piece, the protective cover and the sterile cover may be used to fit over a surface. The surface may be a sterile surface used in a health setting (e.g., a surgical room). In one example, the surface may be a medical tray and/or a surgical tray (e.g., a mayo stand). The protective cover and the sterile cover may be implemented having a size that may fit over a particular model of surgical tray. Different sizes of protective cover and sterile cover combinations may be implemented based on the size of the surface. The shape and/or size of the protective cover and/or the sterile cover may be varied according to the design criteria of a particular implementation.

The sterile cover may be implemented to prevent direct contact of surgical tools with the surface. Generally, the sterile cover may be a thin material (e.g., a thin plastic material). The thin plastic tool may be easily damaged. For example, sharp surgical tools may be capable of accidentally poking through the sterile cover and making contact with the surface. A surgical tool that makes contact with the surface may be considered contaminated. Regulations for medical procedures (e.g., a safety protocol) may provide instructions to dispose of contaminated surgical tools. Replacing contaminated surgical tools may be costly and/or add to preparation time for health workers. The protective cover may be implemented to provide a durable and/or robust material. The durable and/or robust material of the protective cover may shield the sterile cover from the surgical tools. The protective cover may prevent the surgical tools from accidentally poking through the sterile cover and/or touching the surface. For example, a movement and/or force of a surgical tool that may damage and/or tear the sterile cover may be blocked by the protective cover (e.g., the sterile cover may be incapable of withstanding a particular amount of force applied by a sharp edge of one of the surgical tools). By protecting the sterile cover, the surgical tools may be less likely to become contaminated and/or be in need of disposal. For example, by reducing the likelihood of the surgical tools from being contaminated, the protective cover may reduce medical costs (e.g., less waste) and/or reduce preparation time for health workers (e.g., less time spent replacing contaminated tools).

The protective cover may be attached to the sterile cover by binding the sides and a closed end of the sterile cover to the protective cover. In one example, binding only the sides and an unopened end of the sterile cover to the protective cover may provide an inexpensive and efficient method of attaching the two pieces together. Binding the sterile cover and the protective cover together as one piece that may slide onto a surgical tray stand may enable a person to quickly prepare (e.g., stage) a surgical room for a surgical procedure.

Referring to FIG. 1, a diagram illustrating an example embodiment of the present invention is shown. An apparatus 100 is shown. The apparatus 100 may comprise a protective cover 102 and a sterile cover 104. The sterile cover 104 may comprise a portion 106 and a portion 108. The portion 106 may be implemented within the protective cover 102 (e.g., a covered portion). The portion 108 may extend out of the protective cover 102 (e.g., an exposed portion). The exposed portion 108 of the sterile cover 104 may create, provide and/or have an open end 110. Other ends of the sterile cover 104 may be closed.

The protective cover 102 may comprise an open edge 112, a closed edge 114 and two closed edges 116-118. The two closed edges 116-118 may be implemented perpendicular to the open edge 112 and the closed edge 114. The closed edge 114 may be parallel to the open edge 112. In one example, the open edge 112, the closed edge 114 and the two closed edges 116-118 may form a pouch and/or pocket that may contain the covered portion 106 of the sterile cover 104. The exposed portion 108 of the sterile cover 104 may extend out of an open edge 112 of the protective cover 102.

The sterile cover 104 may be a sterile heavy-duty reinforced surgical table cover. The sterile cover 104 may be configured to protect a surface from contamination. For example, the surface may be a medical surface (e.g., a surgical tray). The sterile cover 104 may be disposable. For example, the sterile cover 104 may be tossed out as medical waste after a medical procedure. The sterile cover 104 may be used for various medical purposes. The sterile cover 104 may be a stand cover (e.g., a surgical stand cover).

The sterile cover 104 may comprise a nonwoven fabric. For example, a material of the sterile cover 104 may be a synthetic material and/or a spunbonded, meltblown and spunbonded (SMS) fabric. The sterile cover 104 may be chemically treated (e.g., to provide a barrier against liquids and/or various organisms). The sterile cover 104 may ensure a sterile environment (e.g., for a medical procedure). In one example, the sterile cover 104 may be approximately 23 inches by 54 inches in size. The type of material, the size and/or the shape of the sterile cover 104 may be varied according to the design criteria of a particular implementation.

The protective cover 102 may be configured to protect the sterile cover 104 from being pierced, ripped and/or torn. For example, medical and/or surgical tools that may be placed on a tray surface for a medical procedure. In one example, the medical tools may comprise sharp instruments used for surgery (e.g., a scalpel) that may damage the sterile cover 104. The sterile cover 104 may prevent the medical tools from being contaminated according to a safety standard. The protective cover 102 may prevent sharp edges of the medical and/or surgical tools from making direct contact with the sterile cover 104. For example, the protective cover 102 may prevent a sharp edge of a surgical tool from piercing the sterile cover 104.

The protective cover 102 may be implemented using a robust material. The robust material of the protective cover 102 may provide protection from being pierced by the medical tools. For example, an amount of force that may piece the sterile cover 104 (e.g., causing contamination) may not pierce the protective cover 102. The robust material of the protective cover 102 may be a tightly woven textile. In one example, the robust material of the protective cover 102 may comprise knitted cotton. In another example, the robust material of the protective cover 102 may comprise a cotton-polyester blend. In yet another example, the robust material of the protective cover 102 may comprise a microfiber material and/or a nylon material. In still another example, the robust material of the protective cover 102 may be a tri-laminate fabric. The protective cover 102 may be chemically-treated to provide waterproof and/or fire-retardant properties. The protective cover 102 may be washable and/or re-useable. The particular type of material implemented for the protective cover 102 may be varied according to the design criteria of a particular implementation.

Figure 2:
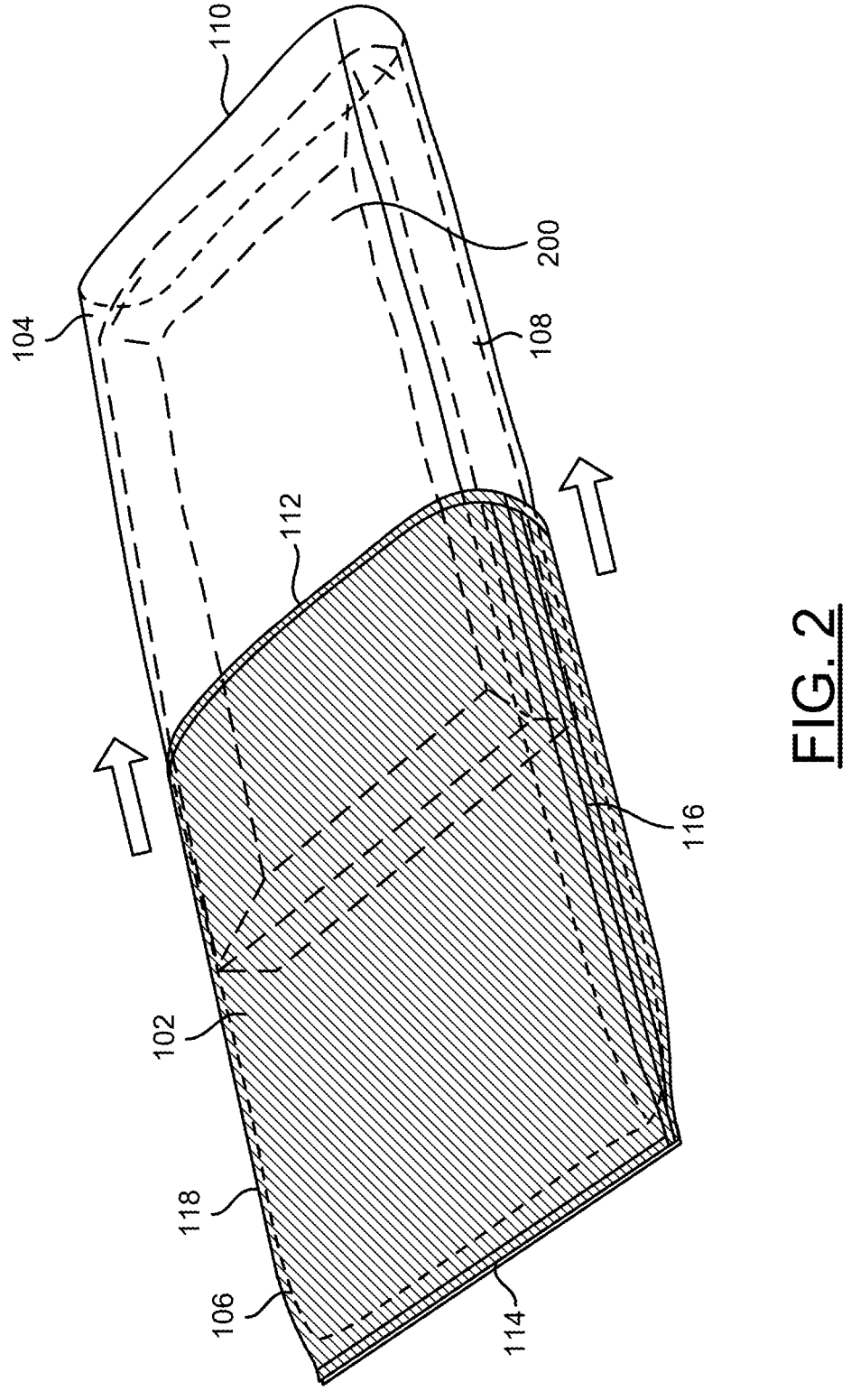
FIG. 2 is a diagram illustrating sliding an example embodiment of the present invention over a tray.

Referring to FIG. 2, a diagram illustrating sliding an example embodiment of the present invention over a tray is shown. The protective cover 102 and the sterile cover 104 are shown. A tray 200 is shown. The protective cover 102 and the sterile cover 104 may be configured to slide onto the tray 200.

The tray 200 may be a surgical tray (or medical tray). For example, the tray 200 may be configured to provide support for medical tools and/or surgical tools. One or more of the medical tools and/or surgical tools may comprise a sharp edge (e.g., an edge capable of piercing the sterile cover 104). The open end 110 of the sterile cover 104 may slide over the tray 200. After the exposed portion 108 of the sterile cover slides over the tray 200, the open edge 112 of the protective cover 102 may slide over the tray 200. The covered portion 106 of the sterile cover 104 along with the protective cover 102 may slide over the tray 200.

In the example shown, the protective cover 102 may be partially over and/or covering the tray 200. The protective cover 102 may continue to slide over the tray 200 (e.g., until the open edge 112 covers all or most of the tray 200). The protective cover 102 may slide over the tray 200 along with the covered portion 106 of the sterile cover 104 until the closed edge 114 touches the end of the tray 200. For example, the protective cover 102 and the sterile cover 104 may act as a sheath and/or casing by covering a top and bottom surface of the tray 200.

Providing the protective cover 102 and the sterile cover 104 as the apparatus 100 may enable a quick and efficient staging for a medical procedure. For example, a medical worker may utilize the open end 110 and the open edge 112 together to quickly slide the apparatus 100 over the tray 200 (e.g., in one motion). Providing the protective cover 102 and the sterile cover 104 may enable a medical worker to collect and/or carry one object instead of two separate objects (e.g., a sterile cover and a separate protective cover). Sliding the apparatus 100 over the tray 200 (e.g., as a casing and/or sheath) may ensure that protective cover 102 and/or the sterile cover 104 may not slide off the tray 200. After sliding the apparatus 100 over the tray 200, the medical tools may be placed on the protective cover 102.

Figures 3, 4:
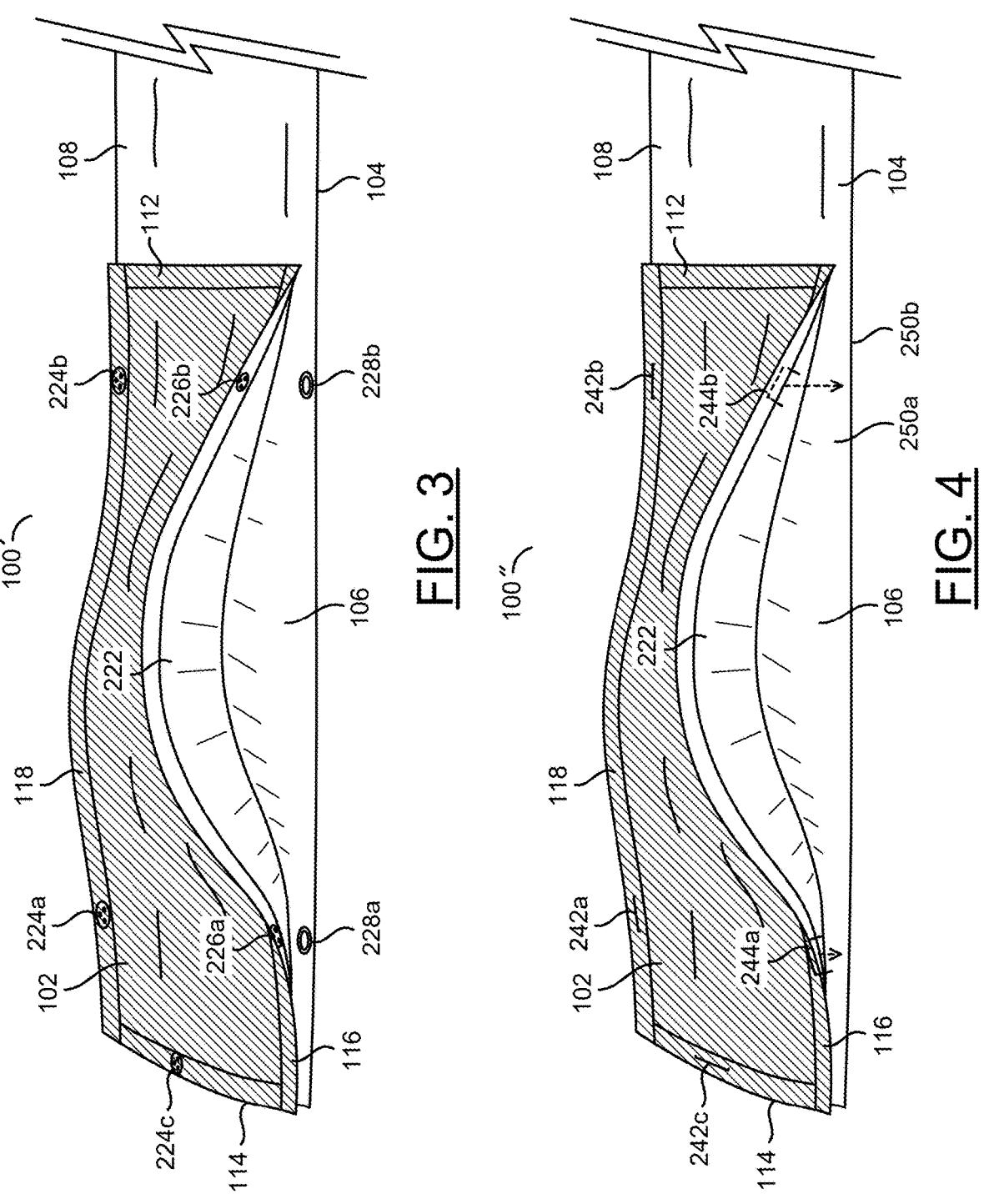
FIG. 3 is a diagram illustrating attaching a protective cover to a sterile cover using a button fastener.
FIG. 4 is a diagram illustrating attaching a protective cover to a sterile cover using staples.

Referring to FIG. 3, a diagram illustrating attaching a protective cover to a sterile cover using a button fastener is shown. An example embodiment of the apparatus 100' is shown. The protective cover 102 may be attached and/or connected to the sterile cover 104. For example, medical workers and/or other workers may prepare the apparatus 100' before a medical procedure by attaching the protective cover 102 to the sterile cover 104. For example, enabling the protective cover 102 to be removably attached to the sterile cover 104 may enable the protective cover 102 to be re-used (e.g., washed, sterilized and then attached to another sterile cover portion).

The apparatus 100' may comprise button fasteners. The button fasteners may be one example of an attachment between the protective cover 102 and the sterile cover 104. An inner surface 222 of the protective cover 102 may implement a number of buttons. Fastened buttons 224a-224c are shown providing the attachment of the protective cover 102 to the sterile cover 104. Unfastened buttons 226a-226b are shown to demonstrate how the protective cover 102 may be attached to the sterile cover 104. In the example shown, one button may be implemented on the closed edge 114 and two buttons may be implemented on each of the closed edges 116-118. The open edge may not benefit from having a button. Other button configurations may be implemented. In one example, the buttons may comprise metal snap buttons. In another example, the buttons may comprise threaded buttons. The number, arrangement and/or type of the buttons used to attach the protective cover 102 to the sterile cover 104 may be varied according to the design criteria of a particular implementation.

The sterile cover 104 may comprise openings configured to secure the buttons (e.g., a female portion of a metal snap or an opening for a threaded button). In the example shown, openings 228a-228b may be representative examples of openings on one side of the sterile cover 104. The buttons may attach the protective cover 102 to the sterile cover 104. In the example shown, the closed edge 114 and the closed edge 118 may be attached to the sterile cover 104 using the fastened buttons 224a-224c. After fastening the protective cover 102 to the sterile cover 104 the buttons may be hidden from view. The closed edge 116 is shown unattached with the sterile cover 104 with the unfastened buttons 226a-226b on the inner surface 222 lining up to the openings 228a-228b of the sterile cover 104. For example, after the unfastened buttons 226a-226b are fastened to the openings 228a-228b, the closed edge 116 may be connected to form a generally closed edge between the protective cover 102 and the sterile cover 104.

In the example shown, the protective cover 102 may comprise a single piece that may be attached on top of the sterile cover 104. For example, when implemented with a single piece, the protective cover 102 may protect a top surface of the tray 200. In some embodiments, the protective cover 102 may comprise two pieces (e.g., a top piece and a bottom piece that may form a pouch for the sterile cover 104). For example, when implemented with two pieces, the protective cover 102 may protect a top surface and a bottom surface of the tray 200.

Referring to FIG. 4, a diagram illustrating attaching a protective cover to a sterile cover using staples is shown. An alternate example embodiment of the apparatus 100" is shown. The protective cover 102 may be attached and/or connected to the sterile cover 104. The alternate example embodiment of the apparatus 100" may have a similar implementation as the button fastener embodiment of the apparatus 100' shown in association with FIG. 3. For example, the alternate example embodiment of the apparatus 100" shown may implement staples to attach and/or connect the protective cover 102 to the sterile cover 104.

The apparatus 100" may comprise staples as fasteners. Staples may be one example of an attachment between the protective cover 102 and the sterile cover 104. In the example shown, connected staples 242a-242c may attach the closed edge 114 and the closed edge 118 to the sterile cover 104. The open edge 112 of the protective cover 102 may not benefit from having a staple.

The closed edge 116 of the protective cover 102 is shown in the process of being attached to the covered portion 106 of the sterile cover 104. Unconnected staples 244a-244b are shown being inserted through the protective cover 102. The unconnected staples 244a-244b are shown extending through the inner surface 222 of the protective cover 102. The unconnected staples 244a-244b may pass through the closed edge 116 of the protective cover 102 and into the sterile cover 104 to create the attachment.

Implementing staples (e.g., the connected staples 224a-242c and/or the unconnected staples 244a-244b) may enable quick attachment between the protective cover 102 and the sterile cover 104. Implementing the staples may enable an attachment without making modifications to the sterile cover 104. For example, to implement the buttons for the apparatus 100' as shown in association with FIG. 3, the sterile cover 104 may be modified to implement respective openings to connect with the buttons. Implementing the staples may interfere with the integrity and/or sterility of the sterile cover 104 (e.g., depending on the safety standard). The size, material and/or type of the staples implemented may be varied according to the design criteria of a particular implementation.

A top face 250a and a bottom face 250b of the sterile cover 104 is shown. In the example shown, the protective cover 102 may comprise a single piece of robust material that may be attached to the top face 250a of the sterile cover 104. For example, the attachment of the protective cover 102 to the sterile cover 104 may comprise connecting the protective cover 102 on the top face 250a of the covered portion 106 of the sterile cover 104. When the protective cover 102 is applied to only the top face 250a, the protective cover 102 may be configured to prevent the top face 250a of the covered portion 106 of the sterile cover 104 from being pierced when a force of a sharp edge of a surgical tool is applied to the protective cover 102. For example, protecting only the top face 250a may reduce costs (e.g., less materials used for the protective cover 102).

In some embodiments, the protective cover 102 may comprise a first piece of the robust material and a second piece of the robust material. For example, the first piece of the robust material of the protective cover 102 may protect the top face 250a of the covered portion 106 of the sterile cover 104 and the second piece of the robust material of the protective cover 102 may protect the bottom face 250b of the covered portion 106 of the sterile cover 104. In some embodiments, both the pieces of the protective cover 102 may be attached together to enclose the covered portion 106 of the sterile cover 104. In one example, the one piece of the protective cover 102 may comprise the unfastened buttons 226a-226b and the other piece of the protective cover 102 may comprise the openings 228a-228b to create the attachment over the sterile cover 104. In another example, one piece of the protective cover 102 may be stapled using the staples 244a-244b to the other piece of the protective cover 102 to create the attachment over the sterile cover 104. In yet another example, both pieces of the of the protective cover 102 may be buttoned to (or stapled to) the sterile cover 104. The type of attachment between the two pieces of the protective cover 102 and the sterile cover 104 may be varied according to the design criteria of a particular implementation.

Other types of attachments may be implemented (e.g., ties, clips, feeding the material of the protective cover through a hole, etc.). The attachments may be configured to enable medical staff to quickly attach the protective cover 102 to the sterile cover 104 without affecting the integrity and/or sterility of the sterile cover 104. The types of attachments implemented may be varied according to the design criteria of a particular implementation.

Figure 5:
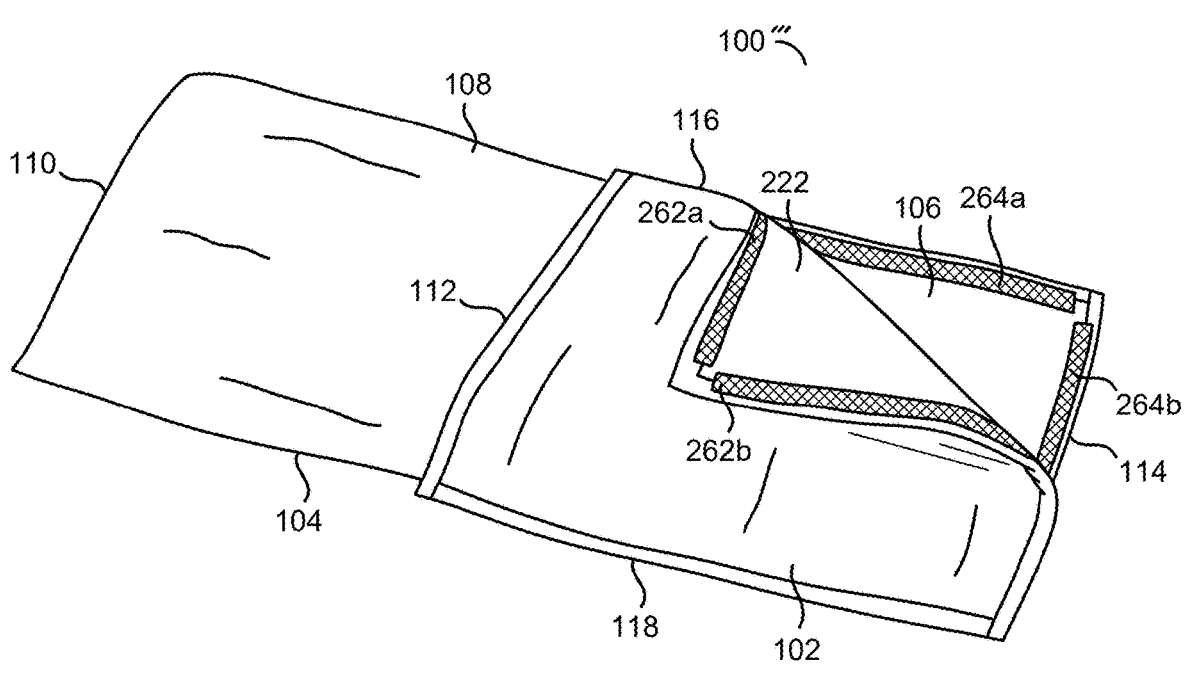
FIG. 5 is a diagram illustrating attaching a protective cover to a sterile cover using an adhesive.

Referring to FIG. 5, a diagram illustrating attaching a protective cover to a sterile cover using an adhesive is shown. An alternate embodiment of the apparatus 100″ is shown. The alternate embodiment of the apparatus 100″ may comprise the protective cover 102 with the covered portion 106 of the sterile cover 104 within the protective cover 102 and the exposed portion 108 of the sterile cover 104 extending out of the open edge 112 of the protective cover 102. Adhesives may be implemented to attach the protective cover 102 to the sterile cover 104.

The inner surface 222 of the protective cover 102 is shown folded back to reveal a section of the covered portion 106 of the sterile cover 104. The inner surface 222 may comprise an adhesive 262a-262b (e.g., adhesive strips) along the closed edge 114 and the closed edge 116. Similarly, an adhesive may be applied to the inner surface 222 of the closed edge 118. Applying the adhesive to the open edge 112 may not be beneficial. An adhesive 264a-264b may be implemented on the covered portion 106 of the sterile cover 104. Applying the adhesive 264a-264b to the exposed portion 108 outside of the protective cover 102 may not be beneficial. In some embodiments, both the adhesives 262a-262b and the adhesives 264a-264b may be implemented. In some embodiments, either the adhesives 262a-262b may be implemented or the adhesives 264a-264b may be implemented (e.g., providing both of the adhesives 262a-262b on the inner surface 222 and the adhesives 264a-264b on the covered portion 106 may not be beneficial). For example, implementing only the adhesives 262a-262b on the inner surface 222 may enable the sterile cover 104 to be used without modification (e.g., off-the-shelf).

The adhesives 262a-262b and/or the adhesives 264a-264b may provide the attachment between the protective cover 102 and the sterile cover 104. In some embodiments of the apparatus 100″, the adhesives 262a-262b and/or the adhesives 264a-264b may be a non-hazardous binding (e.g., a glue). In some embodiments of the apparatus 100″, the adhesives 262a-262b and/or the adhesives 264a-264b may be adhesive strips and/or a double-sided tape. The adhesives 262a-262b and/or the adhesives 264a-264b may comprise a binding material that may be acceptable in an operating room environment. The amount and/or the material used for the adhesives 262a-262b and/or the adhesives 264a-264b may be varied according to the design criteria of a particular implementation.

Figure 6:
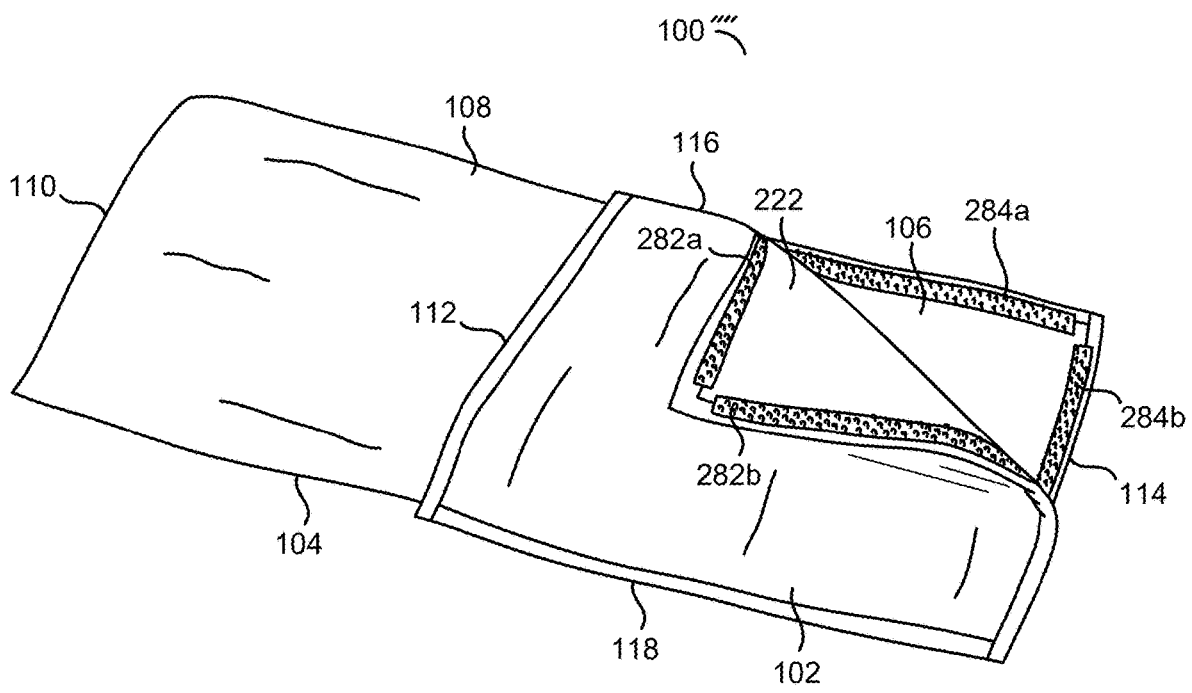
FIG. 6 is a diagram illustrating attaching a protective cover to a sterile cover using hook and loop fasteners.

Referring to FIG. 6, a diagram illustrating attaching a protective cover to a sterile cover using hook and loop fasteners is shown. An alternate embodiment of the apparatus 100‴ is shown. The alternate embodiment of the apparatus 100‴ may comprise the protective cover 102 with the covered portion 106 of the sterile cover 104 within the protective cover 102 and the exposed portion 108 of the sterile cover 104 extending out of the open edge 112 of the protective cover 102. Hook and loop fasteners may be implemented to attach the protective cover 102 to the sterile cover 104.

In some embodiments, the attachment may comprise hooks 282a-282b and respective loops 284a-284b (e.g., together hook and loop fasteners). The inner surface 222 of the protective cover 102 is shown folded back to reveal the covered portion 106 of the sterile cover 104. The inner surface 222 may comprise hook fasteners 282a-282b along the closed edge 114 and the closed edge 116. Similarly, the inner surface 222 may comprise the hook fasteners 282a-282b along the closed edge 118. Applying the hook fasteners 282a-282b to the open edge 112 may not be beneficial. The loop fasteners 284a-284b may be implemented on the covered portion 106 of the sterile cover 104. Applying the loop fasteners 284a-284b to the exposed portion 108 outside of the protective cover 102 may not be beneficial. Attaching the hook fasteners 282a-282b to the respective loop fasteners 284a-284b may provide a secure and removable attachment between the protective cover 102 and the sterile cover 104.

In some embodiments of the apparatus 100‴, the inner surface 222 may comprise the hook fasteners 282a-282b and the covered portion 106 of the sterile cover 104 may comprise the loop fasteners 284a-284b. In some embodiments of the apparatus 100‴, the inner surface 222 may comprise the loop fasteners 284a-284b and the covered portion 106 of the sterile cover 104 may comprise the hook fasteners 282a-282b. Implementing the hook and loop fasteners 282a-282b and 284a-284b may enable a manufacturer to provide the apparatus 100 put together as one piece. Which of the protective cover 102 and/or the sterile cover 104 implements the hook fasteners 282a-282b or the loop fasteners 284a-284b may be varied according to the design criteria of a particular implementation.

Figure 7:
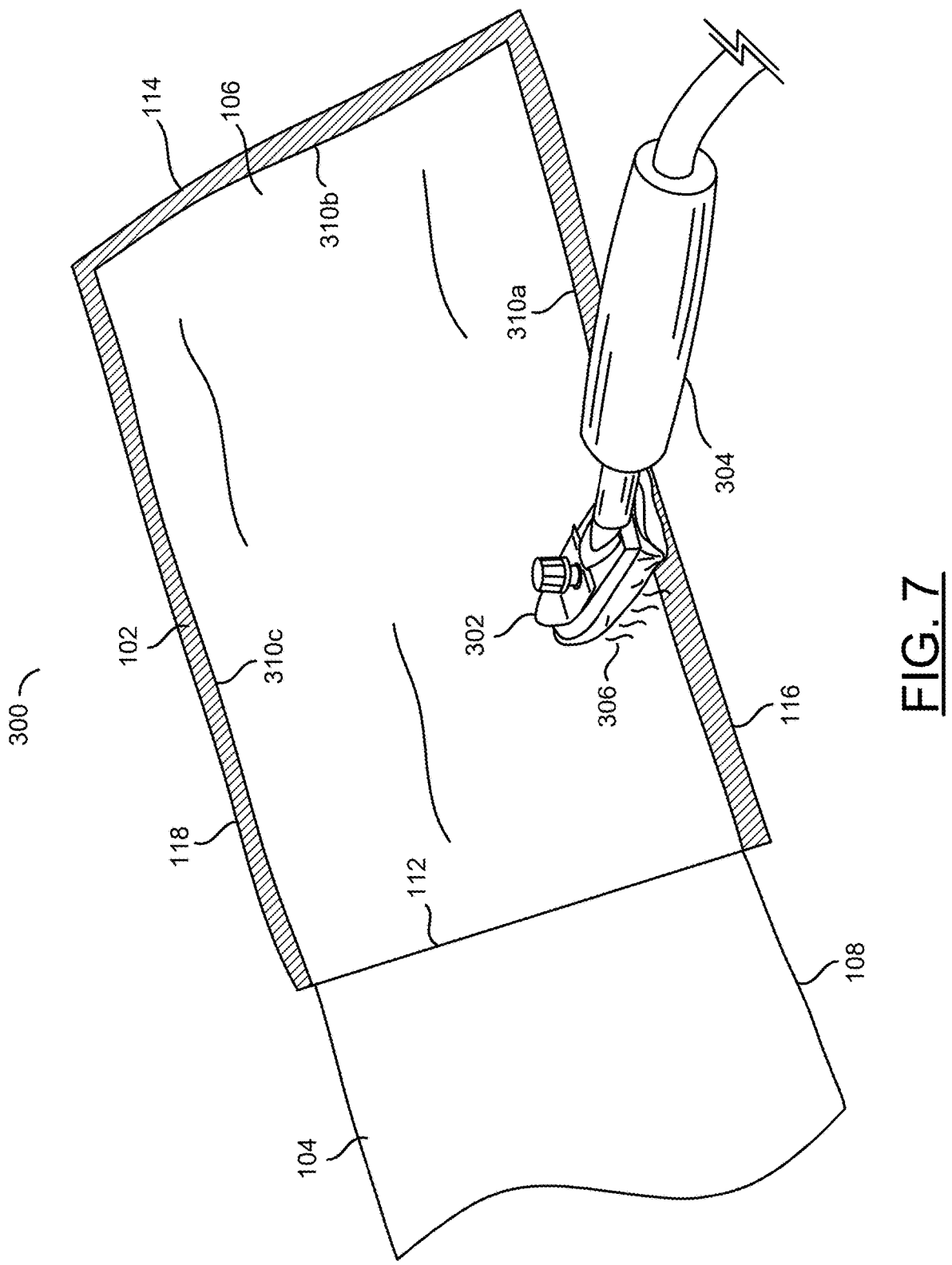
FIG. 7 is a diagram illustrating attaching a protective cover to a sterile cover using a heat source.

Referring to FIG. 7, a diagram illustrating attaching a protective cover to a sterile cover using a heat source is shown. A heat application method 300 is shown. In some embodiments, the attachment between the protective cover 102 and the sterile cover 104 may be implemented by using the heat application method 300. The heat application method 300 may comprise the protective cover 102 and the sterile cover 104 with the covered portion 106 of the sterile cover 104 within the protective cover 102 and the exposed portion 108 of the sterile cover 104 extending from the open edge 112 of the protective cover 102. The closed edge 114 and the two closed edges 116-118 may be attached together using a heat source 302 to enable the covered portion 106 of the sterile cover 104 to be held within the protective cover 102.

The heat source 302 is shown performing the heat application method 300. In the example shown, the heat source 302 may be a heating iron and/or a sealing iron that may comprise a handle 304. Heat 306 is shown being generated by the heat source 302. The heat 306 may be applied by the heat source 302 to the covered portion 106 of the sterile cover 104 and the protective cover 102. In some embodiments, the heat source 302 may be a sealing iron, a clothing iron, a heat press, etc. The particular implementation of the heat source 302 may be varied according to the design criteria of a particular implementation.

In some embodiments, the heat source 302 may apply the heat 306 to specific portions of the apparatus 100. For example, the heat 306 may be applied along the seams 310a-310c to connect the edges of the sterile cover 104 to the closed edges 114-118 of the protective cover 102 (e.g., leaving the central area of the protective cover 102 and the covered portion 106 of the sterile cover 104 loose and/or unattached). The seams 310a-310c may comprise a thin overlay film that may provide an adhesive that enables an attachment of the protective cover 102 to the sterile cover 104 when the heat 306 is applied. The open edge 112 of the protective cover 102 may not be attached to the sterile cover 104 using the heat 306. For example, a person may use the handle 304 to maneuver the heat source 302 along the seams 310a-310c to enable the heat 306 to create the attachment between the sterile cover 104 and the protective cover 102. The temperature of the heat 306 provided and/or the width of the seams 310a-310c may be varied according to the design criteria of a particular implementation.

The two pieces of the apparatus 100 may be put together by the cloth piece (e.g., the protective cover 102) being attached to the sterile cover 104 (e.g., the mayo stand cover) by the heat press 302. For example, the heat application method 300 may be implemented by only binding the sides (e.g., the seams 310a-310c) and the unopened end of the mayo stand cover 104.

In some embodiments of the heat application method 300, the heat source 302 may be implemented as a heat press. In one example, the protective cover 102 may comprise an overlay film (e.g., over all or most of the inner surface 222 of the protective cover 102) and the attachment between the protective cover 102 to the sterile cover 104 may be enabled by the heat source 302. For example, the sterile cover 104 may slide onto a press top (e.g., an ironing board type surface). The open end 110 of the sterile cover 104 may slide on first so that the closed end (e.g., at the seam 310c) may be close (e.g., facing) a person standing in front of the heating press 302. Then the protective cover 102 may be added next by sliding the protective cover 102 over the sterile cover 104. The heating press (e.g., the heat source 302) may be brought down (e.g., manually or automatically with the press of a button) to compress and apply the heat source 306 onto all of the protective cover 102. Applying the heat source 306 to all of the protective cover may enable the overlay film to create the attachment between the protective cover 102 and the sterile cover 104.

Figure 8:
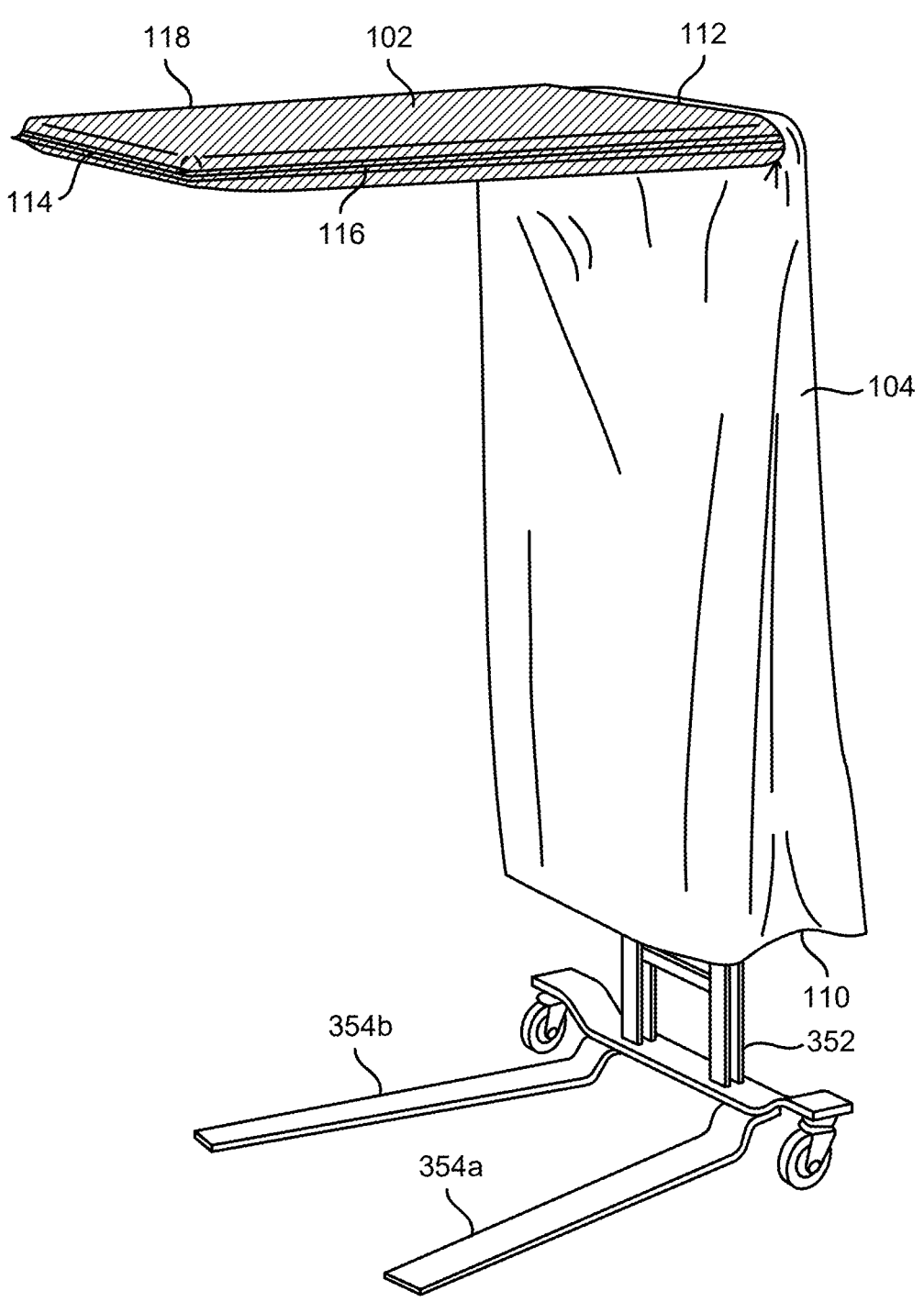
FIG. 8 is a diagram illustrating an example embodiment of the present invention implemented to fit over a surgical tray stand.

Referring to FIG. 8, a diagram illustrating an example embodiment of the present invention implemented to fit over a surgical tray stand is shown. A staged tray 350 is shown. The staged tray 350 may provide an illustrative example of preparation and/or staging performed by a medical worker. For example, the staged tray 350 may be prepared to hold medical tools and/or surgical tools for a medical/surgical procedure.

The staged tray 350 may comprise a tray stand 352 with the apparatus 100. The apparatus 100 is shown covering the tray stand 352. In an example, the tray stand 352 may be a Mayo Stand comprising a small tray (e.g., a surgical tray similar to the tray 200 shown in association with FIG. 2) and two steel foot-operated adjustments 354a-354b. The foot-operated adjustments 354a-354b may be configured to adjust the height of the tray stand 352. In the example shown, the surgical tray 200 may be hidden from view. For example, the protective cover 102 and the covered portion 106 (also hidden from view) may cover the surgical tray 200. The exposed portion 108 of the sterile cover 104 may be draped over an upright portion of the tray stand 352.

To provide the staged tray 350, as shown, a medical worker may insert the open end 110 over the tray portion of the tray stand 352 and slide the exposed portion 108 of the sterile cover 104 down the upright portion of the tray stand 352. The protective cover 102 (with the covered portion 106 of the sterile cover 104) may then slide over the tray 200. For example, the protective cover 102 with the covered portion 106 of the sterile cover 104 may be pulled over a top and bottom surface the tray 200 together until the closed edge 114 reaches an end of the tray 200. With the covered portion 106 within the protective cover 102, a top face and a bottom face of the sterile cover 104 may be protected by the protective cover 102.

The tray 200 may be used to hold surgical instruments. For example, the surgical instruments may be placed on the protective cover 102. The protective cover 102 may prevent the surgical instruments from piercing the sterile cover 104 (e.g., prevent contaminating the surgical instruments).

The terms "may" and "generally" when used herein in conjunction with "is (are)" and verbs are meant to communicate the intention that the description is exemplary and believed to be broad enough to encompass both the specific examples presented in the disclosure as well as alternative examples that could be derived based on the disclosure. The terms "may" and "generally" as used herein should not be construed to necessarily imply the desirability or possibility of omitting a corresponding element.

The designations of various components, modules and/or circuits as "a"-"n", when used herein, disclose either a singular component, module and/or circuit or a plurality of such components, modules and/or circuits, with the "n" designation applied to mean any particular integer number. Different components, modules and/or circuits that each have instances (or occurrences) with designations of "a"-"n" may indicate that the different components, modules and/or circuits may have a matching number of instances or a different number of instances. The instance designated "a" may represent a first of a plurality of instances and the instance "n" may refer to a last of a plurality of instances, while not implying a particular number of instances.

While the invention has been particularly shown and described with reference to embodiments thereof, it will be understood by those skilled in the art that various changes in form and details may be made without departing from the scope of the invention.

The invention claimed is:

1. An apparatus comprising:
    a sterile cover configured to prevent a contamination of a surface; and
    a protective cover configured to (i) fit over a first portion of said sterile cover and (ii) provide protection against a sharp edge piercing said sterile cover, wherein
        (a) said first portion of said sterile cover is within said protective cover,
        (b) a second portion of said sterile cover creates an open end that extends out of an open edge of said protective cover,
        (c) said open end and said open edge enable said sterile cover and said protective cover to slide over a top side and a bottom side of said surface together, and
        (d) an attachment connects said protective cover to said sterile cover,
        (e) said protective cover comprises (i) a first piece of a robust material on a top face of said sterile cover and (ii) a second piece of said robust material on a bottom face of said sterile cover, and
        (f) said attachment comprises connecting said first piece of said robust material to said second piece of said robust material over said first portion of said sterile cover.

2. The apparatus according to claim 1, wherein said surface comprises a medical tray configured to provide support for a medical tool comprising said sharp edge.

3. The apparatus according to claim 2, wherein said contamination of said medical tray supporting said medical tool requires discarding said medical tool according to a safety protocol.

4. The apparatus according to claim 2, wherein said apparatus is used to stage said medical tray and said medical tool for a surgical procedure.

5. The apparatus according to claim 1, wherein said sterile cover is a thin material that is unable to withstand a first amount of force by said sharp edge.

6. The apparatus according to claim 5, wherein said protective cover prevents said sterile cover from being pierced when said first amount of force of said sharp edge is applied to said protective cover.

7. The apparatus according to claim 1, wherein said protective cover comprises said open edge, a closed edge parallel to said open edge and two closed edges perpendicular to said open edge and said closed edge.

8. The apparatus according to claim 1, wherein said contamination of said surface is prevented by sliding said open end of said sterile cover over said top side and said bottom side of said surface such that said surface is inserted into said sterile cover.

9. The apparatus according to claim 1, wherein (i) said sterile cover prevents said contamination of said top side and said bottom side of said surface and (ii) said protective cover provides said protection of a top face and a bottom face of said first portion of said sterile cover.

10. The apparatus according to claim 1, wherein said attachment comprises an adhesive.

11. The apparatus according to claim 1, wherein said attachment comprises a hook and loop fastener.

12. The apparatus according to claim 1, wherein said protective cover comprises an overlay film and said attachment is enabled by a heat source.

13. The apparatus according to claim 12, wherein said heat source is generated by a heat press configured to apply said heat source onto all of said protective cover.

14. The apparatus according to claim 12, wherein said heat source is generated by a heating iron configured to apply said heat source to a seam that creates said attachment between said protective cover and said sterile cover.

\* \* \* \* \*